United States Patent [19]
Kempe et al.

[11] Patent Number: 5,910,554
[45] Date of Patent: *Jun. 8, 1999

[54] HIGHLY CROSS-LINKED POLYMERIC SUPPORTS

[75] Inventors: Maria Kempe, Lund, Sweden; George Barany, Falcon Heights, Minn.

[73] Assignee: Regents Of The University Of Minnesota, Minneapolis, Minn.

[ * ] Notice: This patent is subject to a terminal disclaimer.

[21] Appl. No.: 08/793,212

[22] PCT Filed: Jun. 14, 1996

[86] PCT No.: PCT/US96/10291

§ 371 Date: Jun. 6, 1997

§ 102(e) Date: Jun. 6, 1997

[87] PCT Pub. No.: WO97/00273

PCT Pub. Date: Jan. 3, 1997

Related U.S. Application Data

[63] Continuation-in-part of application No. 08/491,474, Jun. 16, 1995, Pat. No. 5,656,707.

[51] Int. Cl.$^6$ .................................................. C08F 18/00
[52] U.S. Cl. ............................................................ 526/320
[58] Field of Search ............................................. 526/320

[56] References Cited

U.S. PATENT DOCUMENTS

| | | | |
|---|---|---|---|
| 4,908,405 | 3/1990 | Bayer et al. | 525/61 |
| 5,117,009 | 5/1992 | Barany | 549/394 |
| 5,196,566 | 3/1993 | Barany et al. | 560/61 |
| 5,235,028 | 8/1993 | Barany et al. | 528/335 |
| 5,352,756 | 10/1994 | Meldal | 525/50 |
| 5,403,750 | 4/1995 | Braatz et al. | 436/531 |
| 5,656,707 | 8/1997 | Kempe et al. | 526/320 |

FOREIGN PATENT DOCUMENTS

| | | | |
|---|---|---|---|
| 0 510 393 | 10/1992 | European Pat. Off. | B01J 20/32 |
| 3500180 | 7/1986 | Germany | C08F 8/00 |
| 56-138107 | 10/1981 | Japan | A61K 6/08 |
| 60-147419 | 8/1985 | Japan | C08F 220/28 |
| 3-152168 | 6/1991 | Japan | C09D 5/02 |
| WO 92/04384 | 3/1992 | WIPO | C08F 8/00 |
| WO 93/16118 | 8/1993 | WIPO | C08F 283/06 |

OTHER PUBLICATIONS

NIH Grant No. GM 42722 (Abstract).
NIH Grant No. GM 51628 (Abstract).
Albericio et al., "Preparation and Application of the 5–(4–(9–Fluorenylmethyloxycarbonyl)aminomethyl–3, 5–dimethoxyphenoxy)–valeric Acid (PAL) Handle for the Solid–Phase Synthesis of C–Terminal Peptide amides under Mild Conditions," *J. Org. Chem.*, 55, 3730–3743 (1990).
Arshady et al., "Peptide Synthesis. Part 1. Preparation and Use of Polar Supports based on Poly(dimethylacrylamide)," *J. of Chem. Soc. Perkin I*, 2 , 529–537 (1981).
Arshady et al., "Preparation of polymer nano–and microspheres by vinyl polymerization techniques," *J. Microencapsulation*, 5(2), 101–114 (1988).
Arshady et al., "Suspension Polymerization and its Application to the Preparation of Polymer Supports," *Reactive Polymers*, 1, 159–174 (1983).
Atherton et al., "Racemisation of Activated, Urethane–protected Amino–acids by p–Dimethyl–aminopyridine. Significance in Solid–phase Peptide Synthesis," *J.C.S. Chem. Comm.*, 7, 336–337 (1981).
Barany et al., "Solid–phase peptide synthesis: a silver anniversary report," *Int. J. Peptide Protein Res.*, 30 705–739 (1987).
Barany et al., "Novel polyethylene glycol–polystyrene (PEG-PS) graft supports for solid–phase peptide synthesis," *Peptides*, 267–268 (1992).
Barany et al., *The Peptides*, 2, Bookcover, Copyright Page, Table of Contents, Chapter 1 Table of Contents (1979).
Bayer et al., "Immobilized Polyoxyethylene, A New Support for Peptide Synthesis," *Peptides:Structure and Function*, Eds.: V.J. Hruby et al., Proceedings of the 8th American Peptide Symposium, 87–90 (1983).
L. Chen et al., "N–Dithiasuccionoyl (DTS)–Amines:Novel Oxidation Reagents for Intramolecular Disulfide Formations in Peptides Under Mild Conditions," Abstract presented at the *Fourteenth American Peptide Symposium*, Colombus, OH, Jun. 18–23, 1995.

(List continued on next page.)

Primary Examiner—Joseph L. Schofer
Assistant Examiner—N. Sarofim
Attorney, Agent, or Firm—Mueting, Raasch & Gebhardt, P.A.

[57] ABSTRACT

A polymer useful as a solid support for a variety of applications is provided. The polymer is prepared from a composition comprising at least one type of olefinic monomer and a multifunctional (meth)acrylate crosslinker of the following formula (I):

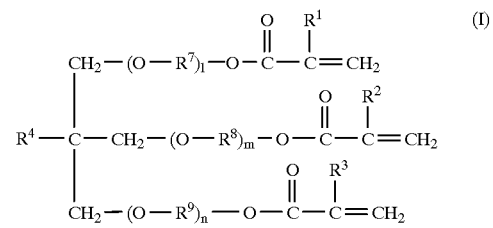

wherein:
(a) $R^1$, $R^2$, and $R^3$ are each independently hydrogen or a methyl group;
(b) $R^4$ is hydrogen or an organic group or substituent that can interact in the polymerization and/or crosslinking process or is nonreactive under the conditions of the polymerization and/or crosslinkling process;
(c) $R^7$, $R^8$, and $R^9$ are each independently —$CH_2$—$CH_2$—, —$CH_2$—$CH_2$—$CH_2$, —$CH_2$—$CH(CH_3)$—, or —$CH(CH_3)$—$CH_2$—;
(d) each of l, m, and n is no greater than about 100 with the proviso that at least one of l, m, or n is at least 1.

24 Claims, 3 Drawing Sheets

OTHER PUBLICATIONS

Colombo, "New Poly(Ethylene Glycol) Supports for the Liquid–Phase Synthesis of Protected Peptide Hydrazides," *Tetrahedron Letters*, 22(41), 4129–4132 (1981).

Drumheller et al., "Multifunctional Poly(ethylene glycol) Semi–Interpenetrating Polymer Networks as Highly Selective Adhesive Substrates for Bioadhesive Peptide Grafting," *Biotechnology and Bioengineering*, 43, 772–780 (1994).

Drumheller et al., "Polymer Networks with Grafted Cell Adhesion Peptides for Highly Biospecific Cell Adhesive Substrates," *Polymeric Networks for Biospecific Substrates*, 380–388 (1994).

Drumheller et al., "Densely Crosslinked polymer networks of poly(ethylene glycol) in trimethylolpropane triacrylate for cell–adhesion–resistant surfaces," *Journal of Biomedical Research*, 29, 207–215 (1995).

Englebretsen et al., "Fmoc SPPS using Perloza™ beaded cellulose," *Int. J. Peptide Protein Res.*, 43, 546–554 (1994).

Hargitai et al., "Polymer–bound chiral polymers for use in enantiomer separations," *Journal of Chromatography*, 540, 145–155 (1991).

Hargitai et al., "Functionalized polymer particles for chiral separation," *J. Chromatogr.*, 630, 79–94 (1993).

Hellerman et al., "Poly(ethylene glycol)s Grafted onto Crosslinked Polystyrenes, $2^{a)}$, Multidetachably Anchored Polymer Systems for the Synthesis of Solubilized Peptides," *Makromol. Chem.*, 184, 2603–2617 (1983).

Hjertberg, "$^{13}$C CP–MAS NMR Study on Content and Mobility of Double Bonds in Poly(trimethylolpropane trimethacrylate)," *Macromolecules*, 23(12), 3080–3087 (1990).

K. Jensen et al., "A Novel Handle Approach for Solid–Phase Peptide Synthesis: Backbone Amide(BAL) Anchoring," Abstract presented at the *Fourteenth American Peptide Symposium*, Colombus, OH, Jun. 18–23, 1995.

Kaiser et al., "Color Test for Detection of Free Terminal Amino Groups in the Solid–Phase Synthesis of Peptides," *Anal. Biochem.*, 34, 595–598 (1970).

Kanda et al., "Synthesis of polyamide supports for use in peptide synthesis and as peptide–resin conjugates for antibody production," *Int. J. Peptide Protein Res.*, 38, 385–391 (1991).

M. Kempe et al., "Novel Highly Cross–Linked Supports for Solid–Phase Peptide Synthesis," Abstract presented at the *Fourteenth American Peptide Symposium*, Colombus,OH, Jun. 18–23, 1995.

Kempe, *Chiral Recognition*, "Studies on chiral discrimination in enzymatic peptide synthesis and non–covalent molecular imprinting," 1–154 (1994).

Kolarz et al., Porous copolymers of trimethylolpropane triacrylate and acrylonitrile, *Makromol. Chem.*, 194, 1299–1306 (1993).

Meldal et al., "Pega: A Flow Stable Polyethylene Glycol Dimethyl Acrylamide Copolymer for Solid Phase Synthesis," *Tetrahedron Lett.*, 33(21), 3077–3080 (1992).

Merrifield, "Solid Phase Peptide Synthesis. I. The Synthesis of a Tetrapeptide," *J. Am. Chem. Soc.*, 85, 2149–2154 (1963).

Reinholdsson et al., "Preparation and properties of porous particles from trimethylolpropane trimethacrylate," *Applied Macromolecular Chem. and Phys.*, 192 113–132 (1991), cited in application at page 10 as *Angew. Makromol. Chem.*.

Reinholdsson, "Poly(tri–methyl propane tri–methacrylate) particles with acid chloride functionaltiy," *Reactive Polymers*, 17, 175–186 (1992).

Reinholdsson, "Poly(tri–methylol propane tri–methacrylate) particles with phosphine functionality," *Reactive Polymers*, 17, 187–195 (1992).

Reinholdsson, "New types of functional composite particles based on poly(tri–methylol propane tri–methacrylate)–preparation, characterization and application," Doctoral Dissertation submitted to Lund University, Sweden, pp. 1–28 (1991).

Renil et al., "Gel–Phase Peptide Synthesis on a New High-–Capacity Tetraethyleneglycol Diacrylate–Crosslinked Polystyrene Support: Synthesis of Pardaxin 16–33," *Tetrahedron*, 50,(22), 6681–6688 (1994).

Rosenberg, et al.,"Macroporous Gels. 3. Copolymerization of Trimethylolpropane Trimethacrylate and Methyl Methacrylate in Toluene of Ethyl Acetate," *Macromolecules*, 20, 1522–1526 (1987).

Sarin et al., "Properties of Swollen Polymer Networks. Solvation and Swelling of Peptide–Containing Resins in Solid–Phase Peptide Synthesis," *J. Am. Chem. Soc.*, 102, 5463–5470 (1980).

Sawicki, "Phase Transfer Catalysts Polyethylene Glycols Immobilized onto Metal Oxide Surfaces," *Tetrahedron Letters*, 23(22), 2249–2252 (1983).

Small et al., "Design and Application of a New Rigid Support for High Efficiency Continuous–flow Peptide Synthesis," *J.C.S. Chem. Commun.*, No. 21, 1589–1591 (1989).

Stewart et al., *Solid Phase Peptide Synthesis*, $2^{nd}$. Ed., Pierce: Rockford, IL, pp. title page, copyright page, table of contents, and pp. 105–106 (1984).

Stewart et al., "Polystyrene–Based Solid Phase Peptide Synthesis: The State of the Art." *Innovation and Perspectives in Solid Phase Synthesis: Peptides, Polypeptides, and Oligonucleotides, Macro–organic Reagents and Catalysts*, Ed.: R. Epton., SPCC UK Ltd., 1–9 (1990).

Zalipsky et al., "Preparation and Use of an Aminoethyl Polyethylene Glycol–Crosslinked Polystyrene Graft Resin Support for Solid–Phase Peptide Synthesis," *Peptides: Structure and Function*, Eds.: V.J. Hruby et al., Proceedings of the 9th American Peptide Symposium, 257–260 (1985).

Zalipsky et al., "Preparation and application of polyethylene glycol–polystyrene graft resin supports for solid–phase peptide synthesis," *Reactive Polymers*, 22, 243–258 (1994.)

Fig. 3

HIGHLY CROSS-LINKED POLYMERIC SUPPORTS

CROSS-REFERENCE TO RELATED APPLICATIONS

This application is a U.S. National Stage application which claims priority to International Application No. PCT/US96/10291 (filed Jun. 14, 1996), which, in turn, is a continuation-in-part of U.S. patent application Ser. No. 08/491,474 (filed Jun. 16, 1995) U.S. Pat. No. 5,656,707 and is incorporated herein by reference.

STATEMENT OF GOVERNMENT RIGHTS

The present invention was made with government support under the National Institutes of Health Grant Nos. GM 42722 and 51628. The government has certain rights in the invention.

BACKGROUND OF THE INVENTION

An increasing array of organic chemical reactions, e.g., acylations, alkylations, enolate additions, Wittig reactions, reductions, oxidations, etc., that are traditionally carried out in homogeneous solution are now being adapted for solid-phase synthesis. For this reason, there is a large demand for suitable polymeric supports. For the most well-studied case, i.e., solid-phase peptide synthesis (SPPS), a wide range of materials have been developed.

Mertifield's original studies, and much subsequent work, used low crosslinked polystyrene [Merrifield, *J. Am. Chem. Soc.*, 85 2149–2154 (1963)]. Polystyrene, however, is limited in the number and variety of solvents that can be used. Because peptide synthesis takes place within a well-solvated gel [Sarin et al., *J. Am. Chem. Soc.* 102 5463–5470 (1980)], one aspect that has been considered in the development of supports for SPPS is how well the material swells. To ensure good swelling properties, most polymeric supports used previously for this purpose have had a minimum amount of crosslinking consistent with mechanical stability. Generally, it is believed that the more crosslinking, the more mechanically stable is the polymer, but the less swellable it is. Thus, polymers used as solid supports have been developed to balance swelling with mechanical stability by using a low level of crosslinker (e.g., typically less than about 10 mole-% and usually only about 1–2 mole-%).

For SPPS, another consideration is to produce a support of the same polarity as the peptide backbone. Sheppard and coworkers developed a polyamide material known commercially as PEPSYN [Arshady et al., *J. Chem. Soc., Perkin Trans. I,* 529–537 (1981)]. This material, however, has not been commercially successful. Another consideration, of particular importance for continuous-flow procedures, is the mechanical stability of the support. Efforts to develop materials for this purpose resulted in PEPSYN K [Atherton et al., *J. Chem. Soc., Chem. Commun.,* 336–337 (1981)] and polyamide-Polyhipe [Small and Sherrington, J. Chem. Soc.. Chem. Commun., 1589–1591 (1989)].

Earlier work in the area of solid-phase synthesis also focused on supports that comprise polyethylene glycol (PEG) grafted onto low crosslinked polystyrene (PS). The resultant PEG-PS can be used in continuous-flow processes, has good swelling properties, and shows good compatibility with peptides [Zalipsky et al., *React. Polym.,* 2, 243–258 (1994), and U.S. Pat. No. 5,235,028 (Barany et al.)]. Solid-phase peptide synthesis procedures and supports are summarized, for example, by G. Barany et al., *Int. J. Peptide Protein Res.* 30 705–739 (1987) and J. M. Stewart et al., *Innovation and Perspectives in Solid Phase Synthesis: Peptides, Polypeptides, and Olizonucleotides. Macroorganic Reagents and Catalysts*, R. Epton, Ed., SPCC UK Ltd., 1–9 (1990).

A need exists for other polymeric supports, particularly for solid- phase synthesis, but also for applications in chromatography, immobilization, etc.

SUMMARY OF THE INVENTION

The polymers of the present invention are prepared from multifunctional oxyacetylene- or oxypropylene-containing (meth)acrylate crosslinkers and optional secondary crosslinkers and olefin-containing monomers, preferably functionalized olefin-containing monomers. The multifunctional (meth)acrylate crosslinkers used in making the highly crosslinked polymers of the present invention are represented by the following formula (I):

wherein $R^1$, $R^2$, and $R^3$ are each independently hydrogen (acrylate) or a methyl group (methacrylate); $R^4$ is hydrogen or an organic group or substituent that can interact in the polymerization and/or crosslinking process or is nonreactive under the conditions of the polymerization and/or crosslinking process; $R^7$, $R^8$, and $R^9$ are each independently —$CH_2$—$CH_2$—, —$CH_2$—$CH_2$—$CH_2$—, —$CH(CH_3)$—$CH_2$—, or —$CH_2$—$CH(CH_3)$—(preferably —$CH_2$—$CH_2$—); and each of l, m, and n is no greater than about 100 with the proviso that at least one of l, m, or n is at least 1 (preferably each of l, m, and n is 1–30, and more preferably l+m+n total 5–25). The crosslinkers are polymerized with one or more olefinic monomers optionally functionalized with amino groups, carboxyl groups, hydroxyl groups, etc. The synthesis of the polymers of the present invention is particularly advantageous because it occurs in one step.

DETAILED DESCRIPTION

The present invention provides highly crosslinked polymers suitable for use in a wide range of applications. For example, the crosslinked polymers of the present invention can be used as solid supports in a variety of solid-phase synthetic applications, as stationary phases in chromatography, and as matrices for immobilization of macromolecules. The polymers of the present invention can be prepared in a wide range of molecular weights. They can also have a wide range of pore sizes, porosities, surface areas, etc., depending on the desired end use. Although they can also be prepared with a wide range of crosslinking, they are preferably highly crosslinked (i.e., prepared using at least about 10 mole-% total crosslinker).

Although the polymers of the present invention are highly crosslinked, they can also possess good swelling properties in various solvents (e.g., dimethylformamide, methylene chloride, acetonitrile, tetrahydrofuran, water, methanol, toluene, ethyl acetate, t-butyl methyl ether, hexane, and trifluoro acetic acid). Preferably, the polymers of the present invention increase in volume by at least about 1.5 times, and more preferably at least about 3 times, in a suitable solvent such as methylene chloride or dimethylformamide. Typically, good swelling properties result from low levels of crosslinking. Thus, the swelling capability of the polymers of the present invention is unexpected. The fact that the polymers swell in both hydrophilic and hydrophobic solvents is highly advantageous, since it extends the range of chemistries that could be conducted on the supports, and it means that biological/biochemical assays of resin-bound compounds are possible.

Also, the polymers of the present invention have generally good compatibility with peptides. That is, they have generally the same polarity, e.g., hydrophobicity/hydrophilicity, as the peptides, which is advantageous in solid-phase peptide synthesis.

The polymers of the present invention are prepared from multifunctional oxyacetylene- or oxypropylene-containing (meth)acrylate crosslinkers, and optional secondary olefin-containing crosslinkers, preferably with an olefin-containing monomer (i.e., olefinic monomer), more preferably a functionalized olefin-containing monomer, and most preferably an amine-functionalized olefin-containing monomer. The multifunctional (meth)acrylate crosslinkers used in making the highly crosslinked polymers of the present invention are represented by the following formula (I):

wherein $R^1$, $R^2$, and $R^3$ are each independently hydrogen or a methyl group; $R^4$ is hydrogen or an organic group or substituent that can interact in the polymerization and/or crosslinking process or is nonreactive under the conditions of the polymerization and/or crosslinking process; $R^7$, R8, and $R^9$ are each independently an ethylene or propylene (normal or isopropylene) group; and each of 1, m, and n is no greater than about 100 with the proviso that at least one of 1, m, or n is at least I (preferably each of 1, m, and n is 1–30, and more preferably I +m +n total 5–25). It should be understood that each of 1, m, and n can be the same or different. If $R^7$, $R^8$, or $R^9$ is an isopropylene group, no directionality is implied. That is, the crosslinker of formula I may include —(O—$CH_2$—CH($CH_3$))$_1$—O—C(O)— or —(O—CH($CH_3$)—)$_1$—O—C(O)—. The multifunctional (meth)acrylate (i.e., acrylate or methacrylate) crosslinker containing one or more oxyacetylene or oxypropylene groups contributes to the unique properties of the polymers of the present invention.

As used herein, an organic group or substituent is non-reactive under the conditions of the polymerization and/or crosslinking process if it does not undergo chemical change or transformation during the reaction and does not prevent the reaction. By this it is meant that the group is selected such that the reactants can react in the manner described. An organic group or substituent interacts in the polymerization and/or crosslinking process if it reacts with the olefinic monomer or other crosslinker molecules to cause chain growth or crosslinking. Suitable $R^4$ groups include substituents such as hydroxyl groups, carboxyl groups, amide groups, ester groups, halogens, amine groups, and the like, as well as alkyl groups, aryl groups, alkaryl or aralkyl groups, alkenyl groups, alkynyl groups, and the like, which can optionally include nonperoxidic oxygen, sulfur, or nitrogen atoms, and be unsubstituted or substituted with the substituents listed above. Preferably, $R^4$ is hydrogen, an oxyacetylene-containing or oxypropylene-containing (meth)acrylate group, an alkyl group, or a hydroxyalkyl group. More preferably, $R^4$ is hydrogen, —$CH_2$—(O—$CH_2$—$CH_2$)$_x$O—C(O)—C($R^5$)=$CH_2$ wherein $R^5$ is hydrogen or methyl group and x is no greater than about 100 (preferably 1–30), a ($C_1$-$C_4$)alkyl group, or a hydroxy($C_1$-$C_4$)alkyl group. Thus, the multifunctional oxyacetylene- or oxypropylene-containing (meth)acrylate crosslinkers can be tri- or tetra-functional acrylates or methacrylates.

Typically, the polymers of the present invention are prepared using a high level of crosslinker (i.e., at least about 10 mole-%, based on the total number of moles of reactants). Preferably, the polymers of the present invention are prepared using at least about 15 mole-% total crosslinker, more preferably at least about 25 mole-%, and most preferably at least about 50 mole-% total crosslinker. The total amount of crosslinker can be as high as 98 mole-% and even up to 100 mole-%, and still produce a polymer with good swelling properties. The total amount of crosslinker includes the multifunctional oxyacetylene- or oxypropylene-containing (meth)acrylate crosslinkers (I) and any optional secondary olefin-containing crosslinkers.

The secondary olefin-containing crosslinkers include any crosslinkers typically used in crosslinking polymers made from olefinic and/or (meth)acrylate monomers. Generally, such crosslinkers are of the formula $H_2C$=CH—$R^6$—HC=$CH_2$ or $H_2C$=C($CH_3$)—$R^6$—($H_3C$)C=$CH_2$, wherein $R^6$ is a divalent organic group, which may be linear, cyclic, or branched containing aromatic and/or aliphatic moieties and optional functionalities such as amide groups, carboxyl groups, nonperoxidic oxygen atoms, and the like. Examples of such secondary crosslinkers include, but are not limited to, divinylbenzene, ethylene glycol dimethacrylate [$H_2C$=C($CH_3$)—C(O)—O—$CH_2$—$CH_2$—O —C(O)—($CH_3$) C=$CH_2$], poly(ethylene glycol-400)-dimethacrylate [$H_2C$=C($CH_3$)—C(O)—(O—$CH_2$—$CH_2$)$_9$—O—C(O)—($CH_3$)C=$CH_2$], N,N'-methylenediacrylamide [$H_2C$=CH—

C(O)—NH—CH$_2$—NH—C(O)—CH=CH$_2$], N,N'-1,4-phenylenediacrylamide [H$_2$C=CH—C(O)—NH—C$_6$H$_4$—NH—C(O)—CH=CH$_2$], 3,5-bis(acryloylamido)benzoic acid [H$_2$C=CH—C(O)—NH—C$_6$H$_3$(CO$_2$H)—NH—C(O)—CH=CH$_2$], and N,O-bisacryloyl-L-phenylalaninol [H$_2$C=CH—C(O)—NH—CH(CH$_2$—C$_6$H$_5$)—CH$_2$—O—C(O)—CH=CH$_2$]. The secondary olefin-containing crosslinker may also be multi-functional (meth)acrylate crosslinkers as in formula I wherein l, m, and n are each 0, such as pentaerythritol triacrylate [formula I wherein l, m, and n each are 0, R$^1$, R$^2$, and R$^3$ are each H, and R$^4$ is an OH group], trimethylolpropane trimethacrylate [formula I wherein l, m, and n each are 0, R$^1$, R$^2$, and R$^3$ are each CH$_3$, and R$^4$ is —CH$_2$CH$_3$ group], and pentaeryiritol tetraacrylate [formula I wherein l, m, and n each are 0, R$^1$, R$^2$, and R$^3$ are each H, and R$^4$ is —CH$_2$—O—C(O)—CH=CH$_2$]. Preferably, the secondary olefin-containing crosslinker is selected from the group consisting of a diacrylate, a dimethacrylate, a diacrylamide, a dimethacrylamide, and a divinylbenzene.

The crosslinkers are copolymerized with one or more olefinic monomers optionally functionalized with amino groups, carboxyl groups, hydroxyl groups, etc. Generally, the functional groups serve as starting points for substituents that will be coupled to the polymeric support. These functional groups can be reactive with an organic group that is to be attached to the solid support or it can be modified to be reactive with that group, as through the use of linkers or handles. The functional groups can also impart various desired properties to the polymer, depending on the use of the polymers. For example, if used in ion exchange chromatography, the polymers of the present invention should include charged groups. If used as supports for peptide synthesis, the polymers of the present invention can include amino groups. Preferably, the polymers of the present invention are made using olefinic monomers containing amino functional groups.

Suitable olefins (i.e., olefmnic monomers) include, for ex-ample, vinyl carboxylic acids such as acrylic acid, methacrylic acid, itaconic acid, and vinylbenzoic acid; vinyl esters such as vinyl acetate, vinyl propionate, and vinyl pivalate; allyl esters such as allyl acetate; allyl amines such as allyl amine and allylethylamine; acrylic esters such as methyl acrylate, cyclohexylacrylate, benzylacrylate, isobomyl acrylate, hydroxybutyl acrylate, glycidyl acrylate, and 2-aminoethyl acrylate; methacrylic esters such as methyl methacrylate, butyl methacrylate, cyclohexyl methacrylate, benzyl methacrylate, ethyl methacrylate, glycidyl methacrylate, and 2-aminoethyl methacrylate; vinyl acid halides such as acryloyl chloride and methacryloyl chloride; styrene and substituted styrenes such as 4-ethylstyrene, 4-aminostyrene, dichlorostyrene, chlorostyrene, 4-hydroxystyrene, hydroxymethylstyrene, 4-hydroxy-3-nitro-styrene, 3-hydroxy-4-metoxy-styrene, and vinylbenzyl alcohol; vinyltoluene; heteroaromatic vinyls such as 1-vinylimidazole, 4-vinylpyridine, and 2-vinylpyridine; mono-functional oxyacetylene-containing (meth)acrylates such as poly(ethylene glycol) ethyl ether methacrylate [H$_2$C=C(CH$_3$)—C(O)—O—(CH$_2$—CH$_2$—O)$_q$—CH$_2$—CH$_3$ wherein q=3–5]; hydroxyl-containing (meth)acrylates such as 3-chloro-2-hydroxypropyl (meth)acrylate and hydroxyalkyl (meth)acrylates wherein the alkyl moiety contains 2–7 carbon atoms (e.g., 2-hydroxyethyl (meth)acrylate, 3-hydroxypropyl (meth)acrylate, 4-hydroxybutyl (meth)acrylate, 2-hydroxybutyl (meth)acrylate, 2-hydroxypropyl (meth)acrylate, 5-hydroxypentyl (meth)acrylate, and 2,3-dihydroxypropyl (meth)acrylate; hydroxyl-containing caprolactone (meth)acrylates such as the ring opening addition products of s-caprolactone with 2-hydroxyethyl (meth)acrylate or 2-hydroxypropyl (meth)acrylate; poly(alkylene glycol)(meth)acrylates such as the ring opening addition products of ethylene oxide and/or propylene oxide with (meth)acrylic acid such as diethylene glycol (meth)acrylate, triethylene glycol (meth)acrylate, and polyethylene glycol methacrylate, and polypropylene glycol methacrylate; hydroxyl-containing (meth)acrylamides such as N-(hydroxymethyl)(meth)acrylamide, N-(1-hydroxyethyl)(meth)acrylamide, N-(2-hydroxyethyl)(meth)acrylamide, N-methyl-N-(2-hydroxyethyl)(meth)acrylamide, N-(1-hexyl-2-hydroxy-1-methylethyl) (meth)acrylamide, N-propyl-N-(2-hydroxyethyl(meth)acrylamide, N-cyclohexyl-N-(2-hydroxypropyl)(meth)acrylamide, α-bromo-N-(hydroxymethyl) acrylamide, and α-chloro-N-(hydroxymethyl)acrylamide); allyl alcohols such as allyl alcohol, 1-buten-3-ol, 1-penten-3-ol, 1-hexen-3-ol, 1-hydroxy-1-vinyl cyclohexane, 2-bromoallyl alcohol, 2-chloroallyl alcohol, 2-methyl-1-buten-3-ol, 2-ethyl-1-penten-3-ol, and I -phenyl-2-propen-1-ol; hydroxyl-containing vinyl ethers such as hydroxyethyl vinyl ether and hydroxybutyl vinyl ethers); and hydroxyl-containing allyl ethers such as allyl-1-methyl-2-hydroxyethyl ether, allyl-2-hydroxypropyl ether, allyl-2-hydroxy-1-phenyl ether, and allyl-2-hydroxy-2-phenyl ether. It should be understood that one or more types of olefinic monomers can be used to make the polymers of the present invention. Depending on the end use, one can choose the desired combination of monomers and the desired type and amount of functionalization.

The polymer of the present invention can be made using optional ingredients such as free-radical initiators (e.g., thermolytic and/or photolytic initiators). Free-radical initiators useful in the present invention include those normally suitable for free-radical polymerization of acrylate monomers. These species include azo compounds, tertiary amines, as well as organic peroxides, such as benzoyl peroxide and lauryl peroxide, and other initiators. Examples of azo compounds include 2,2'-azobis(2-methylbutyronitrile) and 2,2'-azobis(isobutyronitrile). Commercial products of this type include VAZO 67, VAZO 64 and VAZO 52 initiators supplied by E. I. duPont de Nemours & Co. Typically about 0.1–2.0 wt-% is used based upon the total monomer weight.

Preparation of the Polymer

The polymer of the present invention, preferably in the form of particles or beads, can be produced by various methods, including bulk polymerization followed by grinding and sieving, or by emulsion polymerization, dispersion polymerization, suspension polymerization, seeded polymerization, or precipitation polymerization. Such techniques are described in R. Arshady, *J. MicroencaPsulation* 5, 101 (1988), R. Arshady et al., *J. Chem. Soc., Perkins Trans. I,* 529–537 (1981), P. Kanda et al., *Int. J. Pept. Prot. Res.,* 38, 385–391 (1991), and P. Reinholdsson et al., *Angew. Makromol. Chem.,* 192, 113–132 (1991).

Whether a bulk process or a suspension polymerization process, the process is advantageous particularly because functionalized crosslinked polymers can be made in essentially one step. Other functionalized crosslinked polymers are known containing oxyacetylene functionality, however, they are generally grafted polymers prepared from polyethylene glycol. Preferably, the bulk one-step process involves combining one or more types of olefinic monomers with a multifunctional oxyethylene- or oxypropylene-containing (meth)acrylate crosslinker, optionally with a secondary olefin-containing crosslinker and a free-radical initiator, in a suitable solvent. The solvent is one in which the reactants will substantially dissolve, preferably at ambient temperature (i.e., 25–30° C.). By "substantially dissolving" it is meant that the reactants do not have to be completely soluble in the solvent of choice, but they should be sufficiently soluble such that there is enough in solution at the temperature at which the polymerization occurs to effect the polymerization. Suitable solvents include cyclohexanol and higher alcohols, toluene, chloroform, methylene chloride, acetonitrile, tetrahydrofuiran, carbon tetrachloride, benzene, and the like. The reaction is typically carried out in a substantially oxygen-free atmosphere (e.g., in the presence of argon or nitrogen). To initiate the polymerization, the reaction mixture can be exposed to a source of energy, such as ultraviolet radiation and/or an elevated temperature, for a time sufficient to effect the polymerization. Preferably, the reaction is carried out at a temperature of about –30 to about 120° C. (more preferably about 50–90° C.) and exposed to radiation in the wavelength of about 350–370 nm. The polymer can then be crushed and sieved to the desired particle size.

For beads (e.g., substantially spherical particles), any of three generally known suspension polymerization methods can be used. One of these methods uses conventional suspension agents with optional anionic surfactants, another ("limited coalescence method") uses a negatively charged colloidal silica suspending agent and a water-soluble promoter, and a third ("surfactant method") uses a surfactant as a suspending agent, to produce smaller particle sizes. A variety of solvents can be used, such as water or organic solvents such as cyclohexanol. Generally, the choice of solvent, as well as reaction conditions (e.g., temperature), can affect the properties of the polymer (e.g., porosity, pore size, and surface area).

With respect to the first of the three suspension polymerization methods, suspension stabilizers useful in preparing the particles of the present invention are those conventionally used in suspension polymerization processes. The terms "suspension stabilizers," "suspending agents," and "suspension agents" are used interchangeably herein. They may be minimally water-soluble inorganic salts such as those selected from the group consisting of tribasic calcium phosphate, calcium carbonate, calcium sulfate, barium sulfate, barium phosphate, magnesium carbonate, and mixtures thereof. Preferred inorganic suspending agents include those selected from the group consisting of barium sulfate, tribasic calcium phosphate, and mixtures thereof. Water-soluble organic suspending agents, such as those selected from the group consisting of polyvinyl alcohol, poly-N-vinylpyrrolidone, polyacrylic acid, polyacrylamide, and hydroxyalkyl cellulose, can also be used. Surfactants can also be used in this method. Typically, anionic surfactants such as sodium lauryl sulfate, ammonium laureate, and sodium dioctyl sulfosuccinate, are used.

When polymeric particles of less than one micron in diameter are desired, a surfactant or emulsifying agent alone is used as the suspending agent. Surfactants or emulsifiers useful in this "surfactant method" are typically anionic surfactants, cationic surfactants, or nonionic surfactants. Anionic surfactants useful in the present invention include, but are not limited to, the group consisting of alcohol sulfates, alkylaryl sulfonates, ethoxylated alkyl phenol sulfates, ethoxylated alkyl phenol sulfonates and mixtures thereof. Cationic surfactants include, but are not limited to, the group consisting of quaternary ammonium salts wherein at least one higher molecular weight group and two or three lower molecular weight groups are linked to a common nitrogen atom to produce a cation, and wherein the electrically balancing anion is selected from the group consisting of a halide (bromide, chloride, etc.), acetate, nitrite, and lower alkyosulfonate (methosulfate, ethyosulfate, etc.), and mixtures thereof. Nonionic surfactants useful in the present invention include, but are not limited to, the group consisting of ethoxylated alkyl phenols, ethoxylated fatty acids, and ethoxylated fatty alcohols and mixtures thereof. A combination of more than one surfactant or emulsifier is also found to be useful in the invention.

The polymeric particles of the present invention can also be produced by the limited coalescence method. Typically, a reaction mixture of monomers, a negatively charged colloidal silica suspending agent, and a free-radical initiator, are stirred in water under high-speed agitation conditions to break the monomer phase into small droplets. The stirred suspension is heated under nitrogen while polymerization takes place and the desired particles are formed. The particles are collected and washed with water, then dried. The colloidal silica particles have dimensions of about 1–100 nanometers and preferably of about 5–70 nanometers. The size and concentration of these particles controls the size of the polymer particles. Smaller silica particles and higher silica concentration provides smaller bead diameters. Hydrophilic colloidal silica useful as the suspending agent is available commercially, for example, under the tradenames and in the particle sizes as follows: LUDOX TM (20 nm); LUDOX HS (12 nm); LUDOX SM (7 nm); and LUDOX AM (12 nm); all supplied by E. I. duPont de Nemours Company; and NALCO 1060 (60 nm) supplied by Nalco Chemical Company, Oakbrook, Ill.

In this method, the negatively charged colloidal silica suspending agent is preferably used with a water-soluble "promoter" that affects the hydrophobic-hydrophilic balance of the colloidal particles. The components of the promoter are chosen to ensure good water solubility and sufficient complexing with colloidal silica. More specifically, the promoter forms a complex with the suspending agent which is less hydrophilic than the colloidal particles themselves. Although the inventors do not wish to be held to any particular theory, it is believed that the promoter drives the particles of the colloid to the liquid-liquid interface of the oleophilic or hydrophobic droplets and the aqueous medium. As a consequence, the complex is compatible with the hydrophobic or oleophilic monomers dispersed in the aqueous reaction medium. The complex coats the monomer droplets and inhibits their coalescence. Typically, about 0.02–0.5 percent by weight of a promoter is used based on the weight of the aqueous phase. The water-soluble promoter is preferably a low-molecular weight (i.e., about 200 to about 1000 number average molecular weight) organic condensation polymer of a lower alkylene dicarboxylic acid and an alkanol amine (preferably a mono- or dialkanol amine). The dicarboxylic acid can have an alkylene chain having about 2–6 carbon atoms in length. The preferred diacid of this class is adipic acid. The alkanol amine preferably is a lower alkanol amine of which the alkanol groups contain about 1–4 carbon atoms, selected from the group consisting of diethanolamine, 2-amino-2-ethyl-1,3-propanediol, methyl amino ethanol, N-methyldiethanolamine, N-propyldiethanolamine and N-butyldiethanolamine. With adipic acid, these alkanol amines form the polyesters (by which term we also include polyesteramides), such as poly(diethanolamine adipate) and poly(methylamino ethanol adipate). Preferably, the water-soluble promoter is a condensation polymer of adipic acid and diethanolamine.

Also desirable in the polymerization reaction mixture is an inhibitor, i.e., a water-soluble substance to prevent the emulsion or solution polymerization of the monomers in the aqueous phase. Examples of inhibitors include, but are not limited to, those selected from the group consisting of sodium nitrite, copper salts, methylene blue, potassium dichromate, phenols, and mixtures thereof. A preferred example of such a water-soluble polymerization inhibitor is potassium dichromate. Typically about 0.01–0.1 percent by weight of an inhibitor is used based on the total weight of the aqueous phase.

Applications

The polymer of the present invention can be used as a support for a variety of applications. These include, for example, solid-phase synthesis, chromatography (e.g., affinity chromatography, size-exclusion chromatography, ion-exchange chromatography, ion-pair chromatography, normal-phase chromatography, reversed-phase chromatography, and hydrophobic interaction chromatography), and immobilization of macromolecules (e.g., enzymes and antibodies) to increase their stability. The polymeric supports of the present invention have several desirable characteristics for these applications, particularly for solid-phase synthesis: they swell in a variety of solvents; they are stable under the conditions used in most solid-phase syntheses; and they are stable at the pressures experienced in column reactors of continuous-flow systems.

Thus, the polymeric supports of the present invention are useful for solid-phase synthesis in both batch-wise and continuous-flow modes. The fact that the polymeric supports are compatible with automated continuous-flow processes is particularly significant because many commercially available supports for solid-phase synthesis are unusable, or usable only with major difficulties, in this mode.

Solid-phase peptide synthesis typically begins with covalent attachment of a first amino acid (e.g., an "internal reference" amino acid) to the solid support. If the solid support was prepared with amino-functional monomers, the carboxyl group of an N-protected amino acid is covalently linked to a handle moiety which is attached to the amino group on the polymer. A "handle" is defined as a bifunctional spacer which serves to attach the initial amino acid residue to the polymeric support. One end of the handle incorporates a smoothly cleavable protecting group and the other end of the handle couples to the functionalized solid support. Handles which can be used with the present polymers in solid-phase peptide synthesis include, for example acid-labile p-alkoxybenzyl (PAB) handles, photolabile o-nitrobenzyl ester handles, and handles such as those described by Albericio et al., *J. Org. Chem.*, 55, 3730–3743 (1990) and references cited therein, and in U.S. Pat. Nos. 5,117,009 (Barany) and 5,196,566 (Barany et al.). The appropriate handles are coupled quantitatively in a single step onto the amino-functionalized supports to provide a general starting point of well-defined structures for peptide chain assembly. The handle protecting group is removed and the C-terminal residue of the $N^\alpha$-protected first amino acid is coupled quantitatively to the handle. Once the handle is coupled to the solid-phase and the initial amino acid or peptide is attached to the handle, the general synthesis cycle proceeds. The synthesis cycle generally consists of deprotection of the $N^\alpha$-amino group of the amino acid or peptide on the resin, washing, and, if necessary, a neutralization step, followed by reaction with a carboxyl-activated form of the next $N^\alpha$-protected amino acid. The cycle is repeated to form the peptide or protein of interest. Solid-phase peptide synthesis methods using functionalized insoluble supports are well known. Merrifield, *J. Am. Chem. Soc.*, 85, 2149 (1963); Barany and Merrifield, In *Peptides.* Vol. 2, pp. 1–284 (1979); Barany et al., *Int. J. Pentide Protein Res.*, 30, 705–739 (1987). It should be understood that the polymeric materials of the present invention can be used in the solid-phase synthesis of a variety of organic molecules. Peptides are used herein merely as exemplary such molecules.

In one particular embodiment of the present invention, an internal reference amino acid (Fmoc-Nle—OH) was coupled to the free amino groups on the resin particles, followed by deprotection and coupling of the handle Fmoc-5-(4-aminomethyl-3,5-dimethoxyphenoxy)valeric acid (PAL). The challenging sequence 65–74 of acyl carrier protein (ACP) was synthesized successfully on the support by Fmoc-chemistry, using both a conventional solvent (DMF, FIG. 1) and a non-conventional solvent (acetonitrile, FIG. 2) as the reaction media. In addition, H-(Ala)$_{10}$-Val amide (FIG. 3) has been synthesized with results comparable to those obtained on commercially available PEG-PS.

Objects and advantages of this invention are further illustrated by the following examples. The particular materials and amounts thereof recited in these examples as well as other conditions and details, should not be construed to unduly limit this invention. All materials are commercially available from Aldrich Chemical Company, Inc., Milwaukee, Wis., except where stated or otherwise made apparent.

EXAMPLES

Example 1–7

Preparation of Polymers

Example 1

Preparation of poly(trimethylolpropane ethoxylate (14/3 EO/OH) triacrylate-co-poly(ethylene glycol-400)-dimethacrylate-co-2-aminoethyl methacrylate): 2-aminoethyl methacrylate-HCl (0.60 g, 3.6 mmol, obtained from Eastman Kodak, Rochester, N.Y.), poly(ethylene glycol-400)-dimethacrylate (3.88 g, 7.0 mmol), trimethylolpropane ethoxylate (14/3 EO/OH) triacrylate (structure I, 1+m+n approximately 14 (divided among 3 acrylate chains), $R^1$, $R^2$, $R^3$=H $R^4$=$C_2H_5$) (2.74 g, 3.0 mmol) and 2,2'-azobis (isobutyronitrile) (AIBN, 0.1 g, 0.6 mmol, obtained from Pfaltz & Bauer, Waterbury, Conn.) were dissolved in 16 mL of cyclohexanol. The solution, in a KIMAX Screw Cap Culture Tube, was sonicated and then purged with a stream of nitrogen for 5 minutes. The tube was sealed and placed in a RAYONET Photochemical Reactor overnight. The polymerization was initiated by photolytic (350 nm) dissociation of AIBN. The resulting polymer was ground in a mortar and wet-sieved with water through 106 μm and 125 μm sieves. The 106–125 μm fraction was collected and washed with water (acidified with trifluoroacetic acid "TFA" to pH 1–2), and methanol on a sintered glass funnel. The resin (2.66 g) was dried in vacuo overnight. Anal. Found: C, 54.68; H, 7.79; N, 0.70. A portion of the resin was derivatized as described in Examples 8 and 9 with an internal reference and then a handle. The loading of Fmoc-PAL on the resulting resin was 0.25 mmol per gram of resin.

Example 2

Preparation of poly(trimethylolpropane ethoxylate (14/3 EO/OH) triacrylate-co-poly(ethylene glycol-400)- dimethacrylate-co-allylamine): allylamine (0.16 g, 2.75 mmol), poly(ethylene glycol-400)-dimethacrylate (3.88 g, 7.0 mmol), trimethylolpropane ethoxylate (14/3 EO/OH) triacrylate (2.74 g, 3.0 mmol), and AIBN (0.1 g, 0.6 mmol) were dissolved in 12 mL of cyclohexanol. The solution was sonicated, purged with a stream of nitrogen for 5 minutes and then polymerized and processed as described in Example 1 to give 1.88 grams of resin. A portion of the resin was derivatized as described in Examples 8 and 9. The loading of Fmoc-PAL on the resulting resin was 0.11 mmol per gram of resin.

Example 3

Preparation of poly(trimethylolpropane ethoxylate (14/3 EO/OH) triacrylate-co-4-aminostyrene): 4-aminostyrene (0.41 g, 3.45 mmol, obtained from Lancaster, Windham, NH), trimethylolpropane ethoxylate (14/3 EO/OH) triacrylate (8.21 g, 9.0 mmol), and AIBN (0.1 g, 0.6 mmol) were dissolved in 12 mL of cyclohexanol. The solution was sonicated, purged with a stream of nitrogen for 5 minutes, and then polymerized and processed as described in Example 1 to give 2.35 grams of resin. A portion of the resin was derivatized as described in Examples 8 and 9. The loading of Fmoc-PAL on the resulting resin was 0.22 mmol per gram of resin.

Example 4

Preparation of poly(trimethylolpropane ethoxylate (14/3 EO/OH)-co-allylamine): allylamine (0.514 g, 9.0 mmol), trimethylolpropane ethoxylate (14/3 EO/OH) triacrylate (8.208 g, 9.0 mmol), and AIBN (0.1 g, 0.6 mmol) were dissolved in 17.5 mL of cyclohexanol. The solution was sonicated, purged with a stream of nitrogen for 5 minutes and then polymerized and processed as described in Example 1 to give 2.26 g resin. A portion of the resin was derivatized as described in Examples 8 and 9. The loading of Fmoc-PAL on the resulting resin was 0.29 mmol per gram of resin.

Example 5

Preparation of poly(trimethylolpropane ethoxylate (14/3 EO/OH) triacrylate-co-acrylic acid) and amino-functionalized version thereof: acrylic acid (0.25 g, 3.45 mmol), trimethylolpropane ethoxylate (14/3 EO/OH) triacrylate (8.21 g, 9.0 mmol), and AIBN (0.1 g, 0.6 mmol) were dissolved in 12 mL of cyclohexanol. The solution was sonicated, purged with a stream of nitrogen for 5 minutes, and then polymerized and processed as described in Example 1 to give 2.40 grams of resin.

A portion (0.40 g) of this ground and sieved poly (trimethylolpropane ethoxylate (14/3 EO/OH) triacrylate-co-acrylic acid) was treated with N,N'-diisopropylcarbodiimide (40 mg, 0.32 mmol, "DIPCDI" obtained from Advanced ChemTech, Louisville, Ky.) and ethylenediamine (99 mg, 1.64 mmol) in 6 mL of DMF—CH$_2$Cl$_2$ (1:1, v/v) and allowed to react at 25° C. overnight. The polymer particles were washed with dimethylformamide ("DMF"), methanol, acetonitrile and methylene chloride, and then dried in vacuo overnight. The resin was derivatized as described in Examples 8 and 9. The loading of Fmoc-PAL on the resulting resin was 0.15 mmol per gram of resin.

Example 6

Preparation of poly(trimethylolpropane ethoxylate (14/3 EO/OH) triacrylate-co-poly(ethylene glycol) ethyl ether methacrylate-co-2-aminoethyl methacrylate): 2-aminoethyl methacrylate-HCl (0.73 g, 3.6 mmol), poly(ethylene glycol) ethyl ether methacrylate (0.74 g, 16 mmol), trimethylolpropane ethoxylate (14/3 EO/OH) triacrylate (7.30 g, 8.0 mmol), and AIBN (0.1 g, 0.6 mmol) were dissolved in 20 mL of cyclohexanol. The solution was sonicated, purged with a stream of nitrogen for 5 minutes, and then polymerized and processed as described in Example I to give 1.84 gram of resin. Anal. Found: C, 54.86; H, 7.92; N, 0.73. The resin was derivatized as described in Examples 8 and 9. The loading of Fmoc-PAL on the resulting resin was 0.27 mmol per gram of resin.

Example 7

Preparation of poly(trimethylolpropane ethoxylate (14/3 EO/OH) triacrylate-co-methyl methacrylate-co-2-aminoethyl methacrylate): 2-aminoethyl methacrylate-HCl (0.56 g, 3.4 mmol), methyl methacrylate (0.47 g, 4.6 mmol), trimethylolpropane ethoxylate (14/3 EO/OH) triacrylate (7.30 g, 8.0 mmol), and AIBN (0.1 g, 0.6 mmol) were dissolved in 14 mL of cyclohexanol-water (13:1, v/v). The solution was sonicated, purged with a stream of nitrogen for 5 minutes, and then polymerized and processed as described in Example 1. A portion of the resin was derivatized as described in Examples 8 and 9. The loading of Fmoc-PAL on the resulting resin was 0.20 mmol per gram.

Example 8–9

Derivatization of the Polymers (Coupling of "Internal Reference" Amino Acid and Handle) for Solid-Phase Synthesis

Example 8

Coupling of Fmoc-Nle—OH (Fmoc-norleucine; internal reference amino acid) to amino-functionalized resin: Fmoc-Nle—OH (255 mg, 0.72 mmol, obtained from Chem-Index International, Wood Dale, Ill.) in DMF (2 mL), N,N'-diisopropylcarbodiimnide (91 mg, 0.72 mmol) in DMF (0.5 mL), and 1-hydroxy-7-azabenzotriazole (98 mg, 0.72 mmol) in DMF (0.5 mL) were added to 0.6 g of resin and reacted at 25° C overnight. The resin was washed with DMF (5×6 mL) and methylene chloride (5×6 mL). The Fmoc-group was removed from the Fmoc-Nle-resin by treatment with piperidine-DMF (1:4, v/v) for 15+25 minutes, and then again washed with DMF (5 x 6 mL) and methylene chloride (5×6 mL).

Example 9

Coupling of Fmoc-PAL—OH [Fmoc-5—(4-aminomethyl-3,5-dimethoxyphenoxy) valeric acid] to Nle-functionalized resin: Fmoc-PAL-OH (354 mg, 0.72 mmol, Millipore, Bedford, Mass.) in DMF (2 mL), N,N'-diisopropylcarbodiimide (91 mg, 0.72 mmol) in DMF (0.5 mL) and 1-hydroxy-7-zabenzotriazole ("HOAt") (98 mg, 0.72 mmol) in DMF (0.5 mL) were added to 0.6 g of Nle-resin (product of Example 8) and reacted at 25° C. overnight. The resin was washed with DMF (5×6 mL) and methylene chloride (5×6 mL).

Example 10–12: Peptide Synthesis on the Supports

Example 10

Figure 1:
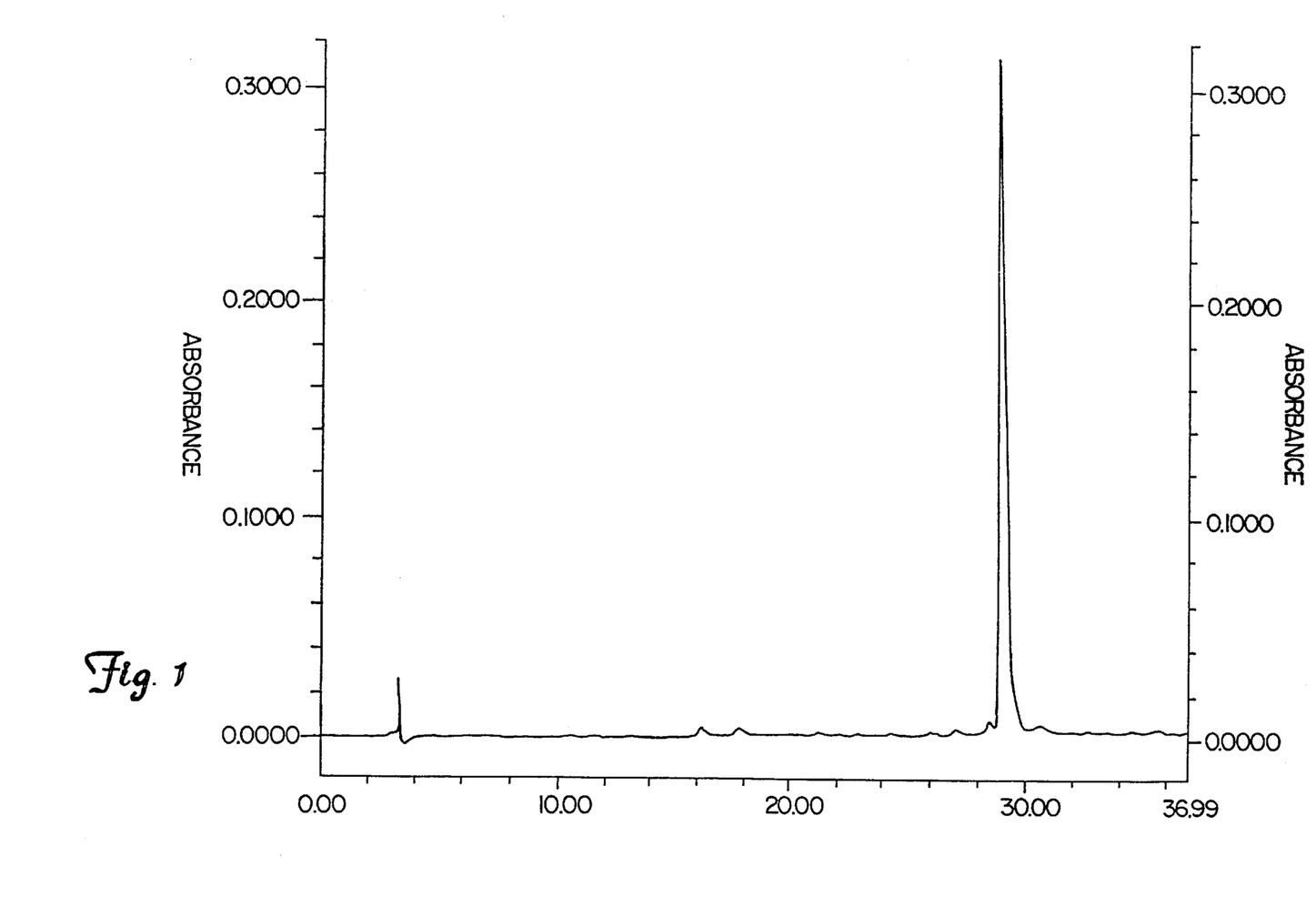
FIG. 1. HPLC chromatogram evaluating crude ACP (65–74) amide preparation described in Example 10. A VYDAC $C_{18}$ reversed-phase column (4.6×250 mm) was eluted at a flow-rate of 1 mL/minute with a linear gradient over 30 minutes from 19:1 to 3:1 of 0.1% TFA in water and 0.1% TFA in acetonitrile. Peptides were detected spectrophotometrically at 220 nm.

Synthesis of acyl carrier protein (ACP) (65–74) amide (H-Val-Gln-Ala-Ala-Ile-Asp-Tyr-Ile-Asn-Gly-NH$_2$) on PAL-Nle-functionalized resin: the synthesis was performed intentionally under non-optimized conditions, in order to emphasize the usefulness of this new class of supports. For this Example 10, Fmoc-PAL-Nle-resin (0.1 g) prepared according to Example 4, was used. Fmoc-removal was achieved with piperidine-DMF (1:4, v/v) for 5+15 minutes (i.e., this was carried out in two steps, one for 5 minutes and one for 15 minutes with the use of fresh piperidine-DMF in the second step). Appropriate $N^\alpha$-Fmoc-amino acids (150 μmol) were each in turn dissolved in DMF (0–4 mL), and 2 hour couplings were each initiated with 150 μmol of 1-hydroxy-7-azabenzotriazole ("HOAt" obtained from Millipore, Bedford, Mass.) dissolved in DMF (0.2 mL) and 150 μmol of N,N'-diisopropylcarbodiimide dissolved in DMF (0.2 mL). All washings between couplings and deprotections were performed with DMF. Cleavage of the peptide was achieved with TFA—$CH_2Cl_2$ (9:1, v/v) (2 mL) for 2.5 hours. The solutions containing cleaved peptides were expressed from the solid-phase reaction vessels with positive nitrogen pressure, and the cleaved resins were washed further with TFA—$CH_2Cl_2$ (9:1, v/v) (3×2 mL). The combined filtrates were evaporated to dryness (including chasing with —$CH_2Cl_2$, 3×3 mL), suspended in water, and lyophilized. The crude peptide was dissolved in 0.1% TFA in water-acetonitrile (1:1), and shown to be 91% pure by high-performance liquid chromatography (FIG. 1). A VYDAC $C_{18}$ reversed-phase column (4.6 x 250 nm) was eluted at a flow-rate of 1 mL/minute with a linear gradient over 30 minutes from 19:1 to 3:1 of 0.1% TFA in water and 0.1% TFA in acetonitrile. Peptides were detected spectrophotometrically at 220 nm.

Example 11

Figure 2:
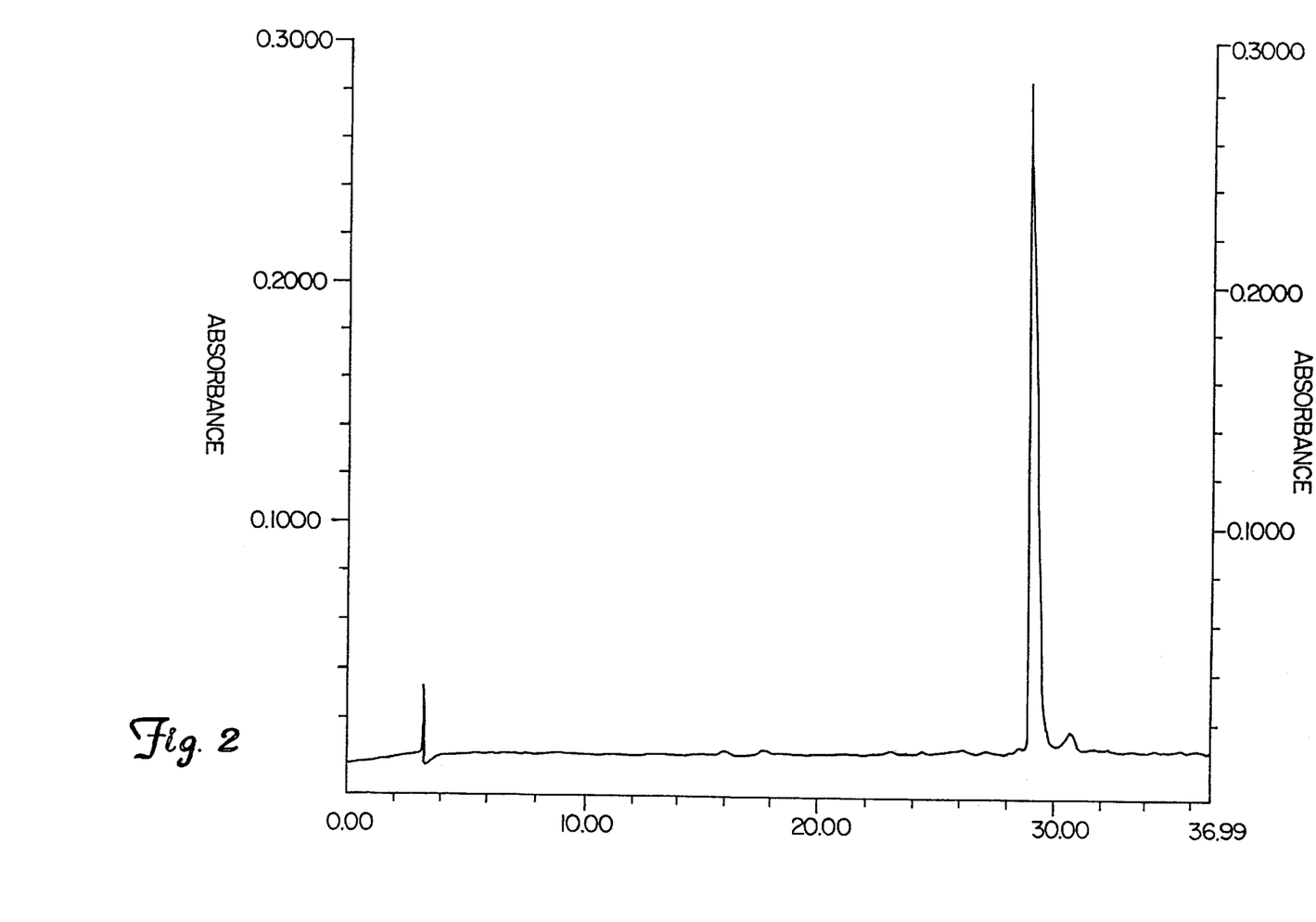
FIG. 2. HPLC chromatogram evaluating crude ACP (65–74) amide preparation described in Example 11. A VYDAC C $_{18}$ reversed-phase column (4.6×250 mm) was eluted at a flow-rate of 1 mL/minute with a linear gradient over 30 minutes from 19:1 to 3:1 of 0.1% TFA in water and 0.1% TFA in acetonitrile. Peptides were detected spectrophotometrically at 220 nm.

Synthesis of acyl carrier protein (ACP) (65–74) amide (H—Val—Gln—Ala—Ala—Ile—Asp—Tyr—Ile—Asn—Gly—$NH_2$) on PAL-Nle-functionalized resin: the synthesis was performed intentionally under non-optimized conditions in a, for peptide synthesis, non-conventional reaction medium (acetonitrile), in order to emphasize the usefulness of this new class of supports. For this Example 11, Fmoc-PAL-Nle-resin (0.1 g) prepared according to Example 4, was used. Fmoc-removal was achieved with piperidine-DMF (1:4, v/v) for 5+15 minutes. Appropriate $N^\alpha$-Fmoc-amino acids (150 μmol) were each in turn dissolved in acetonitrile (0.4 mL, a few drops of DMF was added if needed to dissolve the amino acid derivative), and 2 hour couplings were each initiated with 150 μmol of N,N'-diisopropylcarbodiimide dissolved in acetonitrile (0.4 mL). All washings between couplings and deprotections were performed with acetonitrile. Cleavage of the peptide was achieved with TFA—$CH_2Cl_2$ (9:1, v/v) (2 mL) for 2.5 hours. The solutions containing cleaved peptides were expressed from the solid-phase reaction vessels with positive nitrogen pressure, and the cleaved resins were washed further with TFA—$CH_2Cl_2$ (9:1, v/v) (3×2 mL). The combined filtrates were evaporated to dryness (including chasing with $CH_2Cl_2$, 3×3 mL), suspended in water, and lyophilized. The crude peptide was dissolved in 0.1% TFA in water-acetonitrile (1:1), and shown to be 95% pure by high-performance liquid chromatography (FIG. 2). A VYDAC $C_{18}$ reversed-phase column (4.6×250 mm) was eluted at a flow-rate of 1 mL/minute with a linear gradient over 30 minutes from 19:1 to 3:1 of 0.1% TFA in water and 0.1% TFA in acetonitrile. Peptides were detected spectrophotometrically at 220 nm.

Example 12

Figure 3:
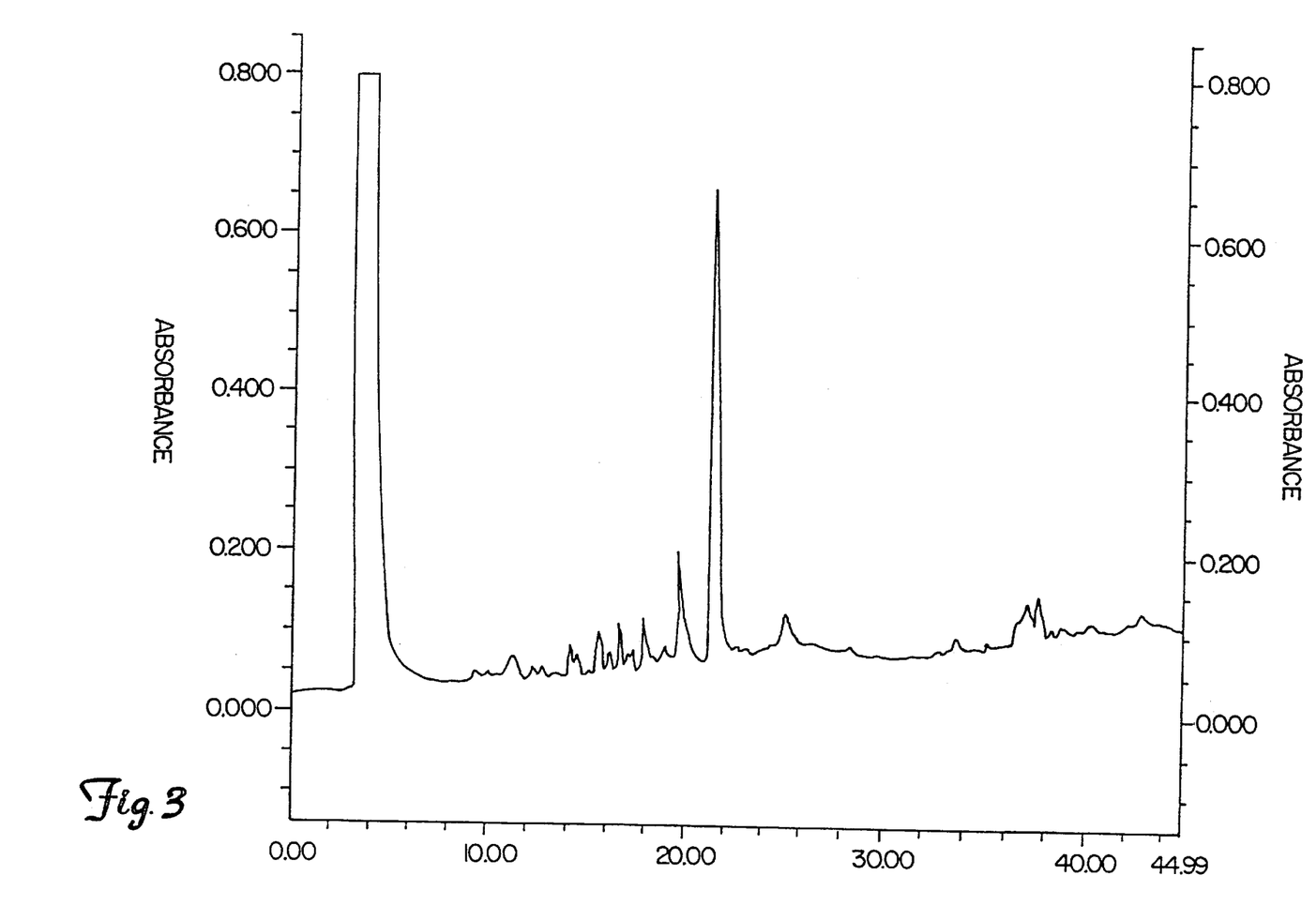
FIG. 3. HPLC chromatogram evaluating crude $(Ala)_{10}$-Val amide preparation described in Example 12. A VYDAC $C_{18}$ reversed-phase column (4.6×250 mm) was eluted at a flow-rate of 1 mL/minute with a linear gradient over 30 minutes from 1:0 to 6:4 of 0.1% TFA in water and 0.1% TFA in acetonitrile. Peptides were detected spectrophotometrically at 220 nm.

Synthesis of deca-alanyl-valine amide (H-$(Ala)_{10}$—Val—$NH_2$) on PAL-Nle-functionalized polymer particles: the synthesis was performed intentionally under non-optimized conditions, in order to emphasize the usefulness of this new class of supports. For this Example 12, Fmoc-PAL-Nle-resin prepared according to Example 1, was used. Fmoc-removal was achieved with piperidine-DMF (1:4, v/v) for 3+17 minutes. Appropriate $N^\alpha$-Fmoc-amino acids (Fmoc-Val-OH and Fmoc-Ala-OH, 120 μmol) in DMF (0.5 mL) were added to 0.1 g resin from Example 1, and 50 minute couplings were initiated with 114 μmol of O-(7-azabenzotriazol-1-yl)-1,1,3,3-tetramethyluronium hexafluorophosphate ("HATU" obtained from Millipore, Bedford, Mass.) in DMF (0.5 mL), 120 μmol of HOAt in DMF (0.5 mL) and 230 μmol of N,N-diisopropylethylamine ("DIEA") in DMF (0.5 mL). Cleavage of the peptide was achieved with TFA-water (9:1, v/v) (2 mL) for 2 hours. The solutions containing cleaved peptides were expressed from the solid-phase reaction vessels with positive nitrogen pressure, and the cleaved resins were washed further with TFA-water (9:1, v/v) (3×2 mL). The combined filtrates were evaporated (including chasing with $CH_2Cl_2$, 3×3 mL), suspended in water, and lyophilized. The crude peptide was dissolved in neat TFA and shown to be 57% pure by high-performance liquid chromatography (FIG. 3). A VYDAC $C_{18}$ reversed-phase column (4.6×250 mm) was eluted at a flow-rate of 1 mL/minute with a linear gradient over 30 minutes from 1:0 to 6:4 of 0.1% TFA in water and 0.1% TFA in acetonitrile. Peptides were detected spectrophotometrically at 220 nm.

The results of Examples 10–12 demonstrate that these supports can be used for the synthesis of peptides that are difficult to make by solid-phase synthesis.

Examples 13–15

Preparation and Derivatization of Polymers in the Form of Beads

Example 13

Spherical beads were prepared by suspension polymerization using a reactor and an overhead stirrer following the designs described by R. Arshady et al., React. Polym., 1, 159–174 (1983). An aqueous phase consisting of deionized water (120 mL; previously purged with a stream of argon for 5 minutes), 1% polyvinyl alcohol in water (6 mL), and ammonium laureate solution (5 mL of 1% lauric acid in water, adjusted to pH 10.3 with concentrated aqueous $NH_4OH$), and an organic phase (which had been purged with a stream of argon for 5 minutes) consisting of allylamine (2.86 g, 50 mmol), trimethylolpropane ethoxylate (14/3 EO/OH) triacrylate (10.94 g, 12 mmol), trimethylolpropane trimethacrylate (1.02 g, 3.0 mmol), AIBN (0.5 g, 3.0 mmol), and toluene (17 mL) were stirred (400 revolutions per minute) under an argon atmosphere for 1 hour at 70° C. The beads were collected on a sintered glass filter funnel, washed with $H_2O$ (approximately 2 L) and MeOH (approximately 300 mL). The beads were sieved, and the major fraction (106–125 μm) was suspended in MeOH and repetitively sedimented and decanted (approximately 10 times) to remove remaining smaller beads. The beads were finally dried in vacuo overnight. Yield: 2.38 g. Anal. Found: C, 55.05; H, 8.11; N, 0.86.

Example 14

Beads were prepared in the same way as those in Example 13, but starting with an organic phase consisting of allylamine (2.86 g), trimethylolpropane ethoxylate (14/3 EOIOH) triacrylate (11.86 g, 13 mmol), AIBN (0.5 g, 3.0 mmol), and toluene (17 mL). Yield: 1.29 g. Anal. Found: C, 54.07; H, 8.15; N, 0.93, consistent with molar incorporation of 8:5 trimethylolpropane ethoxylate triacrylate to allylamine [approximately one-third of the allylamine incorporated provides free amino groups]; note that the polymer is 96% by weight derived from trimethylolpropane ethoxylate tricrylate.

The spherical beads of Examples 13 and 14 contained macropores. Surface area measurements by nitrogen adsorption/desorption indicated that, as with the resins in Examples 1–7, there was no substantial microporous structure.

Example 15

Coupling of Fmoc-PAL—OH to Nle-functionalized beads: Fmoc-Nle-OH (0.64 g, 1.8 mmol) dissolved in DMF (3 mL) was added to beads from Examples 14 and 15 (loadings of free amino groups were 0.2–0.35 mmol/g of beads; 1.0 g per experiment). Coupling in each case was initiated by the addition of HOAt (0.23 g, 1.8 mmol) in DMF (3 mL) followed by DIPCDI (0.25 g, 1.8 mmol) in DMF (3 mL). The mixtures were shaken at 25° C. for 48 hours, and then filtered and washed with DMF (5×15 mL) and $CH_2Cl_2$ (5×15 mL). At this point, the beads were negative to qualitative ninhydrin tests as described in E. Kaiser et al., *Anal. Biochem.*, 34, 595–598 (1970) and J. M. Stewart et al., *Solid Phase Peptide Synthesis*, $2^{nd}$ ed., Pierce: Rockford, Ill. 1984; pp. 105–106. An acetylation step was carried out on the beads using acetic anydride (1 g) in CH2Cl2-pyridine (16 mL, 1:1) for 30 minutes, followed by washing with $CH_2Cl_2$ (5×15 mL) and DMF (5×15 mL). The Fmoc groups were removed by treatment with piperidine-DMF (1:4) (5+15 minutes), followed by washings with DMF (5×15 mL) and $CH_2Cl_2$ (5×15 mL). A solution of Fmoc-PAL-OH (0.89 g, 1.8 mmol) in DMF (3 mL) was added, and the next steps (activation, coupling, acetylation) followed the exact outline given just previously for introduction of Fmoc-Nle-OH.

Examples 16–17

Continuous-Flow Synthesis of Peptides

Example 16

Leu-enkephalinamide (H-Tyr-Gly-Gly-Phe-Leu-$NH_2$) was prepared on derivatized particles of Example 1: Chain assembly was carried out on a Perseptive Biosystems 9050 continuous-flow peptide synthesizer starting with Fmoc-PAL-Nle-resin (0.1 g). $N^\alpha$-Fmoc-amino acids (0.65 mmol each, 5 equivalents) were used with a DIPCDI/HOBt protocol as specified by the manufacturer (30-minutes couplings). HOBt (1-hydroxybenzotriaxole) was obtained from Chem-Impex Int., Wood Dale, Ill. The phenolic sidechain of tyrosine was protected as the tert-butyl ether. Fmoc-removal was achieved with piperidine-DBU-DMF (10:1:39) (6 minutes). DBU (1,8-diazabicylco[5.4.0]undec-7-ene) was obtained from Aldrich Chemical Company. The amino acid composition of the completed peptide-resin was: Gly 2.06, Leu 0.92, Tyr 0.98, Phe 1.00, Nle 1. 16. The peptide-resin was transferred to a syringe reactor. Cleavage of the peptide from the resin was achieved with TFA—$CH_2Cl_2$ (9:1) for 2 hours at 25° C. The filtrate was expressed from the 20 vessel with positive nitrogen pressure, and the cleaved resin was washed (3×1.5 mL) with further TFA—$CH_2Cl_2$ (9:1). The combined filtrates were evaporated to dryness (including chasing 3× with $CH_2Cl_2$), suspended in water, and lyophilized. The cleavage yield was 74% based on amino acid analyses of peptide resins before and after cleavage. The crude peptide was shown to be 25 96% pure by HPLC. The amino acid composition of the crude peptide was: Gly 2.03, Leu 1.01, Tyr 0.98, Phe 0.98. Leu-enkephalin has a calculated exact mass of 554.2853. FABMS, m/z, positive $[M+H]^+$: 555.3; negative $[M-H]^-$: 553.2; [M–H+ TFA]$^-$:667.2.

Example 17

Human gastrin-I (pGlu-Gly-Pro-Trp-Leu-Glu-Glu-Glu-Glu-Glu-Ala-Tyr-Gly-Trp-Met-Asp-Phe-$NH_2$) was prepared on derivatized particles of Example 1: Chain assembly was carried out on a PerSeptive Biosystems 9050 continuous-flow peptide synthesizer, starting with Fmoc-PAL-Nle-resin (0.3 g, 0.26 mmol/g). Na-Fmoc-amnino acids (0.63 mmol each, 8 equivalents) with a BOP/HOBt/NM protocol as specified by the manufacturer (1 hour couplings). BOP (benzotriazolyl N-oxytris(dimethylamino) hexafluorophosphate phosphonium) was obtained from Advanced ChemTech, Louisville, Ky. and NMM (N-methylmorpholine) was obtained from Fisher Scientific, Fair Lawn, N.J. The β- and γ-carboxyl functions of aspartic and glutamic acids were protected as their tert-butyl esters, and the phenolic side chain of tyrosine as the tert-butyl ether. Fmoc removal was achieved with piperidine-DBU-DMF (10:1:39) (6 minutes). The amino acid composition of the completed peptide resin was: Asp 1.1 1, Glu 4.51, Pro 1.09, Gly 1.89, Ala 1.41, Met 1.23, Leu 1.03, Tyr 1.30, Phe 1.43, Nle 1.70. The resin was transferred to a syringe reactor. Cleavage of the peptide from the resin was achieved in a reaction vessel with reagent R: TFA-thioanisole- 1,2-ethanedithiol-anisole (90:5:3:2) (1.5 mL). The filtrate was expressed from the vessel with positive nitrogen pressure, and the cleaved resin was washed with further reagent R (3×1 mL). Ice-cold ethyl ether (8 mL) was then added to the combined filtrates to induce cloudiness. The mixture was maintained at 5° C. for 10 minutes and then centrifuged to collect a white precipitate, which was washed further with ether (3×5 mL), dissolved in water, and lyophilized. The cleavage yield was 60% based on amino acid analyses of peptide-resins before and after cleavage. The crude material was evaluated by analytical HPLC and amino acid analysis: Asp 1.37, Glu 4.68, Pro 1.04, Gly 1.96, Ala 1.31, Met 1.22, Leu 0.94, Tyr 1.24, Phe 1.24. A portion of the crude material (5 mg) was dissolved in 5 mL of 0.1% aqueous TFA and applied to an Alltech/Applied Science Econosil $C_{18}$ (10 $\mu$) preparative HPLC column (10×250 mm) and eluted at 4.5 mL/minutes with a linear gradient over 28 minutes from 7:3 to 2:3 of 0.1% aqueous TFA and 0.1% TFA in acetonitrile. The eluent of the major peak was collected, lyophilized and characterized by analytical HPLC (FIG. 5b) and amino acid analysis: Asp 1.24, Glu 5.91, Pro 1.39, Gly 2.14, Ala 0.90, Met 0.80, Leu 0.79, Tyr 0.92, Phe 0.90. Human gastrin-I has a calculated average mass $[M+H]^+$ of 2099.25 and the observed average mass by FABMS was 2099.7.

While this invention has been described in connection with specific embodiments, it should be understood that it is capable of further modification. The claims herein are intended to cover those variations which one skilled in the art would recognize as the chemical equivalent of what has been described herein. Thus, various omissions, modifications, and changes to the principles described herein may be made by one skilled in the art without departing from the true scope of the invention which is indicated by the following claims.

What is claimed:

1. A polymer prepared from a composition comprising a multifunctional (meth)acrylate crosslinker of the following formula (I):

wherein:

(a) $R^1$, $R^2$, and $R^3$ are each independently hydrogen or a methyl group;

(b) $R^4$ is hydrogen or an organic group or substituent that can interact in the polymerization and/or crosslinking process or is nonreactive under the conditions of the polymerization and/or crosslinking process;

(c) $R^7$, $R^8$, and $R^9$ are each independently —$CH_2$—$CH_2$—, —$CH_2$—$CH_2$—$CH_2$—, $CH_2$—$CH(CH_3)$—, or —$CH(CH_3)$—$CH_2$—; and (d) each of l, m, and n is no greater than about 100 with the proviso that at least one of l, m, or n is at least 1.

2. The polymer of claim 1 prepared from a composition further comprising an olefinic monomer.

3. The polymer of claim 2 wherein the olefinic monomer is functionalized with an amino group.

4. The polymer of claim 3 wherein the amino functionalized olefinic monomer is allylamine, 2-aminoethyl methacrylate, or 4-aminostyrene.

5. The polymer of claim 1 wherein each of l, m, and n is 1–30.

6. The polymer of claim I wherein the multifunctional (meth)acrylate crosslinker is used in an amount of at least about 10 mole-%.

7. The polymer of claim 1 wherein the multifunctional (meth)acrylate crosslinker is used in an amount of at least about 25 mole-%.

8. The polymer of claim 1 wherein the composition further comprises a secondary olefin-containing crosslinker.

9. The polymer of claim 8 wherein the secondary crosslinker is selected from the group consisting of a diacrylate, a dimethacrylate, a diacrylamide, a dimethacrylamide, and a divinylbenzene.

10. The polymer of claim 1 which is in the form of beads.

11. A method of preparing a crosslinked polymer comprising:

(a) combining an olefin-containing monomer and a multifunctional (meth)acrylate crosslinker in a solvent, wherein the multifunctional (meth)acrylate crosslinker has the following formula (I):

wherein:

(i) $R^1$, $R^2$, and $R^3$ are each independently hydrogen or a methyl group;

(ii) $R^4$ is hydrogen or an organic group or substituent that can interact in the polymerization and/or crosslinking process or is nonreactive under the conditions of the polymerization and/or crosslinking process;

(iii) $R^7$, $R^8$, and $R^9$ are each independently —$CH_2$—$CH_2$—, —$CH_2$—$CH_2$—$CH_2$—, —$CH_2$—$CH(CH_3)$—, or —$CH(CH_3)$—$CH_2$—; and (iv) each of l, m, and n is no greater than about 100 with the proviso that at least one of l, m, or n is at least 1; and (b) exposing the mixture to conditions to effect polymerization.

12. The method of claim 11 wherein the mixture is exposed to ultraviolet radiation.

13. The method of claim 11 wherein the mixture further includes a free-radical initiator.

14. The method of claim 11 wherein the olefin-containing monomer is functionalized.

15. The method of claim 14 wherein the olefin-containing monomer is functionalized with an amino group.

16. The method of claim 15 wherein the amino functionalized olefinic monomer is allylamine, 2-aminoethyl methacrylate, or 4-aminostyrene.

17. The method of claim 11 wherein the multifunctional (meth)acrylate crosslinker is used in an amount of at least about 10 mole-%.

18. The method of claim 11 wherein the polymerization is carried out at a temperature of about –30 to about 120° C.

19. The method of claim 11 wherein the polymer is prepared in the form of beads.

20. A method of synthesizing an organic molecule on a solid polymeric support comprising:

(a) providing a solid polymeric support prepared from a composition comprising a multifunctional (meth)acrylate crosslinker of the following formula (I):

wherein:

(i) $R^1$, $R^2$, and $R^3$ are each independently hydrogen or a methyl group;

(ii) $R^4$ is hydrogen or an organic group or substituent that can interact in the polymerization and/or crosslinking process or is nonreactive under the conditions of the polymerization and/or crosslinking process;

(iii) $R^7$, RW, and $R^9$ are each independently —$CH_2$—$CH_2$—, —$CH_2$—$CH_2$—$CH_2$—, —$CH$,—$CH(CH_3)$—, or —$CH(CH_3)$—$CH_2$—; and (iv) each of l, m, and n is no greater than about 100 with the proviso that at least one of l, m, or n is at least 1; and (b) attaching an organic group to the solid polymeric support at the functional group site.

21. The method of claim 20 wherein the organic group of step (b) is an amino acid.

22. The method of claim 20 wherein the solid polymeric support is prepared from a composition further comprising a functionalized olefinic monomer.

23. The method of claim 22 wherein the functionalized olefinic monomer is an amino functionalized olefinic monomer.

24. The method of claim 20 which is carried out in a continuous-flow system.

* * * * *

UNITED STATES PATENT AND TRADEMARK OFFICE
CERTIFICATE OF CORRECTION

PATENT NO.: 5,910,554
DATED: June 8, 1999
INVENTOR(S): Kempe et al.

It is certified that error appears in the above-identified patent and that said Letters Patent is hereby corrected as shown below:

Column 1, lines 57-58, delete "J. Chem. Soc., Chem. Commun." and insert --*J. Chem. Soc., Chem. Commun.*--.

Column 17, line 38, delete "I" and insert --1--.

Column 18, line 62, delete "RW", and insert --$R^8$--.

Column 18, line 63, delete "-CH,-CH" and insert ---$CH_2$-CH --.

Signed and Sealed this

Eighth Day of May, 2001

Attest:

NICHOLAS P. GODICI

Attesting Officer

Acting Director of the United States Patent and Trademark Office